United States Patent [19]

Harris

[11] 4,324,760
[45] Apr. 13, 1982

[54] HYDROGEN DETECTOR

[75] Inventor: Lawrence A. Harris, Schenectady, N.Y.

[73] Assignee: General Electric Company, Schenectady, N.Y.

[21] Appl. No.: 249,791

[22] Filed: Apr. 1, 1981

[51] Int. Cl.³ .................... G01N 31/06; G01N 27/40; G01N 27/12
[52] U.S. Cl. ................. 422/98; 324/71 SN; 338/34; 422/95
[58] Field of Search .................. 422/94–98; 23/232 E; 338/34; 324/71 SN

[56] References Cited

U.S. PATENT DOCUMENTS 3,479,257 11/1969 Shaver ............................... 422/95
3,999,947 12/1976 Mohara et al. .................... 422/95
4,058,368 11/1977 Svensson et al. .................. 23/254

OTHER PUBLICATIONS

Yamamoto et al., "Surface Science", vol. 92, (Feb. 11, 1980), pp. 400–406.

Primary Examiner—Ronald Serwin
Attorney, Agent, or Firm—Jane M. Binkowski; James C. Davis, Jr.; Joseph T. Cohen

[57] ABSTRACT

A hydrogen detector comprised of a substrate supporting an electrically conducting base metal film, an electrically conducting top film of metal able to dissociate hydrogen into atomic form, a polycrystalline film of titanium dioxide sandwiched between the base and top films, the polycrystalline titanium dioxide film electrically insulating the base film from said top film, the base film being in electrical contact with the titanium dioxide film, an insulating layer electrically insulating said titanium dioxide film from said top film except for a predetermined surface portion thereof in electrical contact with said top film, said predetermined electrically contacting portion being at least sufficiently large to produce a measurable electrical conductance, said top and base films being connected to an external circuit to measure conductance, the electrical conductivity of said hydrogen detector varying with the concentration of hydrogen in the atmosphere surrounding it.

12 Claims, 4 Drawing Figures

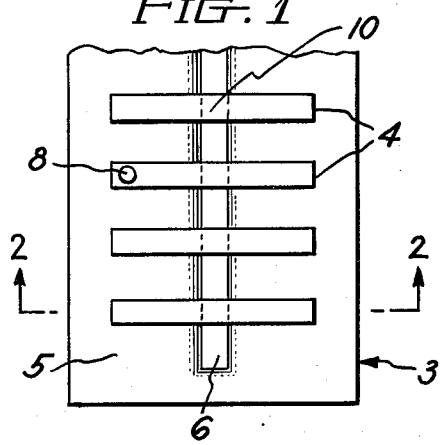
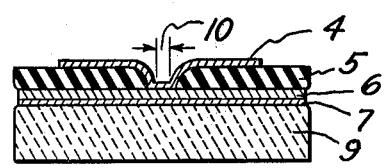
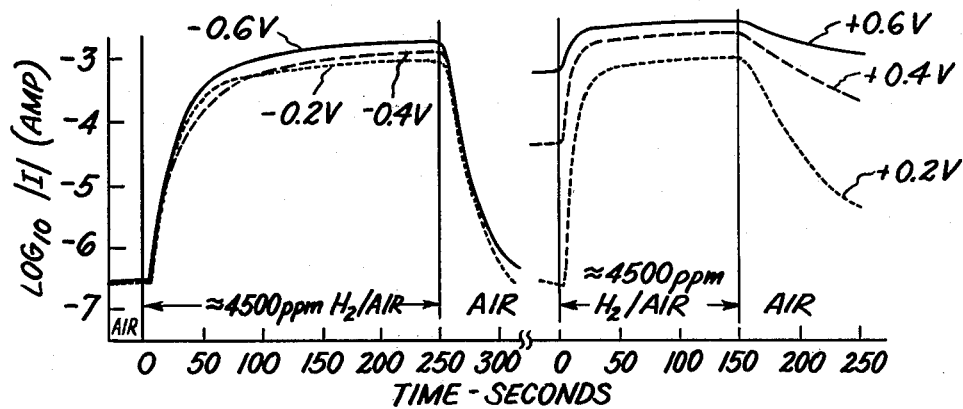
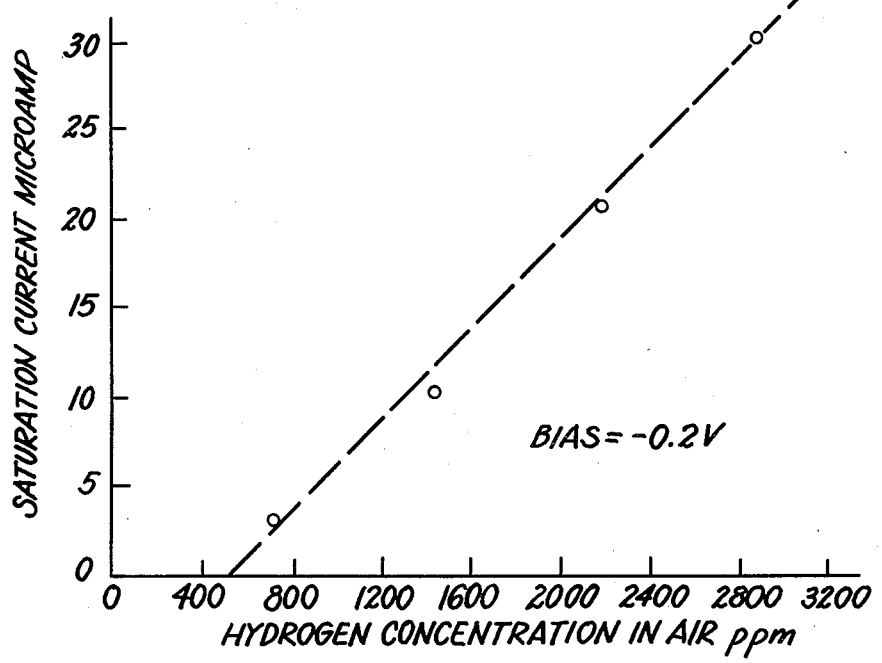

HYDROGEN DETECTOR

This invention relates to a hydrogen detecting device with an electrical conductance influenced strongly by the hydrogen content of the surrounding atmosphere.

The many industrial and possibly future domestic uses for hydrogen require simple sensitive means for detecting hydrogen leaks or for measuring hydrogen concentrations. Current research efforts on production of hydrogen by decomposition of water (by chlorophyll and other organometallic substrates) also demand simple and sensitive means for detecting minute quantities of hydrogen.

Thin film semiconductor hydrogen detectors have been described by several workers in the past. These detectors exhibited a marked increase in surface conductivity in the presence of hydrogen. Though extremely sensitive to hydrogen, the detectors also responded to other materials such as carbon dioxide, benzene, ethanol, and hydrazine, ammonia, and hydrogen sulfide as well as other materials. They also had to be operated at temperatures generally above 250° C.

The present invention provides a simple, reliable, hydrogen detector that does not respond strongly to other gases and that is operable at room temperature. In the present detector excess carriers are introduced by absorption of hydrogen, but electrical conductance is measured through the films instead of along the surface of a film. Since this device depends on the presence of donors in the bulk instead of adsorbed on the surface, it is substantially more selective toward hydrogen.

Briefly stated, the present hydrogen detector is comprised of a substrate supporting an electrically conducting base metal film, an electrically conducting catalytic top film of metal able to dissociate hydrogen into atomic form, a polycrystalline film of titanium dioxide ($TiO_2$) sandwiched between the base and top films, the $TiO_2$ film electrically insulating the base film from said top film, the base film being in electrical contact with the titanium dioxide film, an insulating layer electrically insulating said titanium dioxide film from said top film except for a predetermined surface portion thereof in electrical contact with said top film, said predetermined electrically contacting portion being at least sufficiently large to produce a measurable electrical conductance, said top and base films being connected to an external circuit to measure conductance, the electrical conductance of said hydrogen detector varying with the concentration of hydrogen in the atmosphere surrounding it.

Those skilled in the art will gain a further and better understanding of the present invention from the detailed description set forth below, considered in conjunction with the figures accompanying and forming a part of the specification, in which:

BRIEF DESCRIPTION OF THE DRAWINGS

FIG. 1 is a plan view of one form of a series of the present detectors;

FIG. 2 is a cross sectional view of one of the detectors of FIG. 1 taken along the line 2—2;

FIG. 3 shows the response and recovery of the present detector to 0.45% hydrogen in air at room temperature; and FIG. 4 shows the dependency of saturation current on hydrogen concentration in air for the present detector with −0.2 volts applied at 82° C.

A plan view of one form of the present detector 3 is shown in FIG. 1. FIG. 2 shows a cross sectional view of the detector of FIG. 1 taken along line 2—2. Specifically, in detector 3 electrically insulating or non-insulating substrate 9 supports a base film of metal 7. A polycrystalline film of $TiO_2$ 6 is sandwiched between base film 7 and top metal film 4 and electrically insulates base film 7 from top metal film 4. Insulating layer 5 electrically insulates $TiO_2$ film 6 from top film 4 except for a predetermined effective portion 10 where $TiO_2$ film 6 is in electrical contact with top film 4. Electrical contact 8 on top film 4 and an electrical contact (not shown) on base film 7 are used to electrically connect top film 4 and base film 7 to an external circuit for measuring conductivity.

The substrate preferably is electrically insulating. For example, it can be made of a material such as glass, quartz, a ceramic such as alumina or a plastic such as polystyrene. However, the metal used as the base metal film could be made thicker so that it also could be used as a supporting substrate. Its thickness affects primarily the recovery time, i.e. the period of time required to restore the detector to its original state after hydrogen is removed from its surrounding atmosphere.

The substrate should have a surface suitable for supporting the present films, and preferably, such surface is planar and smooth. To promote adherence of the film, the substrate should be cleaned in a conventional manner before being used. For best results, it should be degreased, for example, by dipping in acetone. Also, preferably, the supporting surface of the substrate is sputter etched.

The base metal film 6 must be sufficiently thick to be electrically conducting. Generally, the base metal film ranges in thickness from about 100 Å to about 1000 Å, and preferably, from about 200 Å to about 500 Å. Films thicker than about 1000 Å provide no significant advantage and may slow recovery time. The base film of metal is preferably selected from the group consisting of titanium, gold, silver, nickel, indium, tin, copper and alloys thereof. Most preferably, it is titanium.

Likewise, the top film of metal 4 must be sufficiently thick to be electrically conducting but not so thick as to slow response time significantly. Generally, its thickness ranges from about 100 Å to about 1000 Å, and preferably, from about 200 Å to about 500 Å. Preferably, the top film of metal is selected from the group consisting of platinum, palladium and alloys thereof.

The polycrystalline film of titanium dioxide 7 should be sufficiently thick and integral to be electrically insulating but not so thick as to slow the response time significantly. Generally, its thickness ranges from about 500 Å to about 5000 Å, but preferably, from about 1000 Å to about 3000 Å.

A number of conventional techniques can be used to deposit or form the base metal film, the titanium dioxide film and the top metal film. Representative of these techniques are sputtering and vapor deposition.

The insulating layer 5 between the top metal film 4 and the $TiO_2$ film 6 need only to be sufficiently thick to be electrically insulating. It can be formed of any insulating material which has no significant deteriorating effect on the hydrogen detector. Representative of the materials useful for forming the insulating layer are lacquer or other polymer film-forming material and silicon monoxide. The insulating layer can be deposited and formed in a conventional manner depending on the material itself. For example, it can be brushed on and, if necessary, treated with thermosetting means, or in the case of materials such as silicon monoxide, by vapor deposition.

The insulating layer 5 electrically insulates the $TiO_2$ film 6 from top metal film 4 except for a predetermined effective portion 10 where $TiO_2$ film 6 is in electrical contact with top metal film 4. The atoms produced by dissociation of hydrogen in top metal film 4 travel through this electrically contacting portion 10 into $TiO_2$ film 6. Therefore, this electrically contacting portion 10 should be at least sufficiently large to be effective, i.e., it should be at least sufficiently large to produce a measurable electrical conductance. As the electrically contacting portion 10 is increased, electrical conductance of the detector is increased but the probability of a short circuit due to a defect in a film is also increased. Generally, this contacting portion 10 between $TiO_2$ film 6 and top metal film 4 ranges from about 2 square millimeters (mm) to about 8 square mm, and typically, it is about 5 square mm.

A small voltage is applied between the base metal and the top catalytic metal films and the current measured. The current increases markedly in the presence of hydrogen. The dc voltages required for operation of the present detector are generally smaller than those available from batteries, so that appropriate series resistors, doubling as current sensing elements, would be needed if the detectors are battery-operated. Nevertheless, low- and moderate-frequency ac methods are also applicable so that a considerable variety of instrumentation circuitry can be devised.

The present detector is operable through a wide range of temperatures, and it is particularly useful from about room temperature up to about 300° C. The response rate, but not the sensitivity, is strongly increased by a moderate rise in temperature. Temperatures above about 300° C. might come dangerously close to effecting a permanent reduction of the $TiO_2$ to a highly conducting state.

The present detectors or devices are effective detectors of hydrogen at concentrations of a few hundred parts per million in air, though some units have detected less than 1/10 of this value with slower response. At very low hydrogen concentrations, the detector responses can be quantitative but they saturate at concentrations above about 0.5% $H_2$ in air, making them excellent alarm devices specific to hydrogen. (Though the detector does not respond to pure $CH_4$, natural gas apparently has sufficient hydrogen in it to produce a strong response.)

Response rate depends on the amount of hydrogen present in the surrounding atmosphere. For pure hydrogen it is less than about one second.

The preferred mode of operation is with a Pt film negative with respect to a base film of Ti. This provides a greater dynamic range and considerably faster recovery when hydrogen is removed. This polarity also makes the detector virtually unresponsive to other gases at room temperature, and almost so even at higher temperatures.

The diffusion of hydrogen into and out of the detector appears to be quite reversible. Air or oxygen is generally needed to remove hydrogen from the detector once the source of $H_2$ is cut off.

Significant advantages of the present detector are its effectiveness as an alarm for hydrogen, operable at room temperature and requiring simple circuitry that uses negligible power in the absence of hydrogen.

The invention is further illustrated in the following examples:

EXAMPLE 1

A series of hydrogen detectors was prepared having the construction shown in FIGS. 1 and 2 except that a polycrystalline film of $TiO_2$ also was deposited between the substrate 9 and the base film 7. It was thought that this film of $TiO_2$ would be useful in anchoring the subsequently deposited films to the glass slide substrate, but other experiments showed that this anchoring $TiO_2$ film was not necessary.

Before use, the glass slide substrates were degreased and cleaned in a conventional manner. Specifically, the detectors were made by successive depositions of thin films on standard glass microscope slides. Each slide was about 75 mm. long and about 25 mm. wide. The first film was a 3000 Å layer of $TiO_2$ sputter deposited onto the clean dry slide. This layer was covered by a 1000 Å film of Ti metal which, in turn, was covered by a second sputter deposited layer of $TiO_2$ in thicknesses ranging from 500 to 3000 Å. The sputtering was done in an rf system in argon for Ti and in 50% argon, 50% $O_2$ for $TiO_2$. The pressure was approximately 2.5 Pa (18–20 microns) and the deposition rate was approximately 90 Å/min. X-ray diffraction showed the films to be principally anatase, with a trace of rutile.

All of the above films covered the entire slide except for two small areas of Ti metal left uncovered near the ends of the slide for contacts to that film.

A coating of lacquer (Hunt Waycoat negative photoresist) was painted by hand over the second $TiO_2$ layer, except for a 2–3 mm strip down the center of the slide and the two Ti contact areas. After this coating was thoroughly dried and polymerized by exposure to uv light, a series of platinum cross strips, 200 Å thick, 1 mm wide and 18 mm long was evaporated, i.e. this vapor deposition was carried out in a conventional manner in a vacuum using an electron beam to evaporate platinum from a crucible.

Each cross strip of platinum, where it comes in contact with the exposed $TiO_2$ layer constitutes one hydrogen detector. Thus a number of independent detectors were formed on each microscope slide.

Each of the detectors was tested by attaching leads to the Ti and Pt films with indium solder, after first applying contact pads of silver paint. A potentiostat (Pine Instruments Co. RDE 3) acted as a regulated power supply and current converter. For logarithmic current plots, a Kiethley Model 26000 Logarithmic Picoammeter in series with a resistor measured the output voltage of the potentiostat's current indicator. The voltages (V) applied for testing were roughly scaled with $TiO_2$ layer thickness (d) to keep the average field (V/d) less than about $10^5$ V/cm. The platinum and titanium films of each detector were electrically conducting, and the $TiO_2$ film sandwiched between the platinum and titanium films was electrically insulating in the absence of hydrogen. In what follows, the voltage or bias is that of the Pt film with respect to the Ti film.

The detector slides were mounted inside a jar or a small metal oven through which the test gas could be flowed and then vented to air. When the oven was used, the slide rested on a thin stainless steel tray to which a Chromel-Alumel alloy thermocouple was attached.

The test gas was made by mixing hydrogen with air through a two-stage dilution system consisting of valves and flow meters. The mixed gas passed through a drying (Drierite) tube and a small 3-way valve mounted near the test chamber. This arrangement allowed the gas flow to be diverted to the room while it was adjusted to the desired mixture and, after the feed lines had equilibrated, the gas was directed to the test chamber. Hydrogen was mixed with air because it was found that the current decreased very slowly after hydrogen removal if oxygen was not present in the ambient gas.

To the extent possible, the flow rate through the test chamber was held at about 2.5 SCFH ($\approx 20$ cm$^3$/sec) as indicated by the flow meters. At this rate, the largest test chamber had a complete change of gas in about 12 sec. All of the measurements were made under dc or slow sweep conditions (100 mV/sec).

The detector having a 1000 Å thick TiO$_2$ film sandwiched between the platinum and titanium films was used in FIG. 3. FIG. 3 shows the current response and recovery time for exposure of the detector to 4500 ppm (0.45%) of hydrogen in air at room temperature for several negative and positive biases. FIG. 3 shows that the response when H$_2$ is introduced is quicker for positive bias than for negative, but the converse is clearly true with respect to recovery.

The detector having a 1000 Å thick TiO$_2$ film between the Pt and Ti films was used in FIG. 4. FIG. 4 shows the dependence of saturation current on H$_2$ concentration in air with $-0.2$ V applied at 82° C.

This steady-state response, now observable at elevated temperature, was approximately linearly dependent on H$_2$ concentration, as FIG. 4 shows, down to about 500 ppm. Below this level the response was not easily detectable. These data were obtained with negative bias only, as that was judged to be the more useful mode of operation.

The detector having a 1000 Å thick TiO$_2$ film between the Pt and Ti films was subjected to 0.09% H$_2$ in air at 23° C., 49° C. and 82° C. using $-0.2$ V. The response time decreased significantly with increase in temperature from several hundred seconds at 23° C. to about 10 seconds at 82° C.

The detector having a 3000 Å thick TiO$_2$ film between the Pt and Ti films was subjected to hydrogen and showed a large increase in current for both polarities in a manner similar to that shown in FIG. 3 which is for a 1000 Å TiO$_2$ film.

EXAMPLE 2

A series of detectors was prepared in the same manner as set forth in Example 1 except that no anchoring TiO$_2$ film was used, i.e. the detector had the structure shown in FIGS. 1 and 2. The thickness of the TiO$_2$ film sandwiched between the Pt and Ti films was 3000 Å. The TiO$_2$ film was electrically insulating and the Ti and Pt films were electrically conducting. The Ti film was in electrical contact with the TiO$_2$ film and the Pt film was in electrical contact only with a portion of the TiO$_2$ film as shown in FIG. 2 and as in Example 1.

The behavior of these detectors was generally similar to the detectors of Example 1 using a 1000 Å thick TiO$_2$ film between the Pt and Ti films.

In Ser. No. 249,790 for "Hydrogen Detector" filed of even date herewith in the name of L. A. Harris, assigned to the assignee hereof and incorporated herein by reference, there is disclosed a hydrogen detector comprised of a substrate supporting an electrically conducting base metal film, an upper electrically conducting diffusion barrier metal film, a polycrystalline film of titanium dioxide sandwiched between the base and diffusion barrier films, the TiO$_2$ film electrically insulating the base film from said diffusion barrier film, the base film being in electrical contact with the titanium dioxide film, an insulating layer electrically insulating said titanium dioxide film from said diffusion barrier film except for a predetermined surface portion thereof in electrical contact with said diffusion barrier film, said predetermined electrically contacting portion being at least sufficiently large to produce a measurable electrical conductance, an electrically conducting or non-conducting catalytic top film of metal able to dissociate hydrogen into atomic form in electrical contact with said diffusion barrier film and at least substantially coextensive with said diffusion barrier film throughout said predetermined electrically contacting portion, said top film when it is electrically conducting or said diffusion barrier film and said base film being connected to an external circuit to measure conductance, the electrical conductance of said hydrogen detector varying with the concentration of hydrogen in the atmosphere surrounding it.

What is claimed is:

1. A hydrogen detector comprised of a substrate supporting an electrically conducting base metal film, an electrically conducting top film of metal able to dissociate hydrogen into atomic form, a polycrystalline film of titanium dioxide sandwiched between the base and top films, said polycrystalline titanium dioxide film electrically insulating the base film from said top film, the base film being in electrical contact with the titanium dioxide film, an insulating layer electrically insulating said titanium dioxide film from said top film except for a predetermined surface portion thereof in electrical contact with said top film, said predetermined electrically contacting portion being at least sufficiently large to produce a measurable electrical conductance, said top and base films being electrically connected to an external circuit to measure conductance, the electrical conductance of said hydrogen detector varying with the concentration of hydrogen in the atmosphere surrounding it.

2. The hydrogen detector according to claim 1 wherein said base metal film is selected from the group consisting of titanium, gold, silver, nickel, tin, copper and alloys thereof.

3. The hydrogen detector according to claim 1 wherein said top metal film is selected from the group consisting of platinum, palladium and alloys thereof.

4. The hydrogen detector according to claim 1 wherein said top metal film is platinum and said base metal film is titanium.

5. The hydrogen detector of claim 1 wherein said insulating layer is comprised of polymer.

6. The hydrogen detector of claim 1 wherein said insulating layer is comprised of silicon monoxide.

7. A hydrogen detector comprised of an electrically conducting metal substrate supporting a polycrystalline film of titanium oxide, an electrically conducting top film of metal able to dissociate hydrogen into atomic form, said polycrystalline film of titanium dioxide being sandwiched between the substrate and top film and electrically insulating the substrate from said top film, the substrate being in electrical contact with the titanium dioxide film, an insulating layer electrically insulating said titanium dioxide film from said top film except for a predetermined surface portion thereof in electrical contact with said top film, said predetermined electrically contacting portion being at least sufficiently large to produce a measurable electrical conductance, said substrate and said top film being electrically connected to an external circuit to measure conductance, the electrical conductance of said hydrogen detector varying with the concentration of hydrogen in the atmosphere surrounding it.

8. The hydrogen detector according to claim 7 wherein said substrate is selected from the group consisting of titanium, gold, silver, nickel, tin, copper and alloys thereof.

9. The hydrogen detector according to claim 7 wherein said top metal film is selected from the group consisting of platinum, palladium and alloys thereof.

10. The hydrogen detector according to claim 7 wherein said top metal film is platinum and said substrate is titanium.

11. The hydrogen detector of claim 7 wherein said insulating layer is comprised of polymer.

12. The hydrogen detector of claim 7 wherein said insulating layer is comprised of silicon monoxide.

* * * * *